United States Patent [19]

Goel

[11] Patent Number: 4,757,125

[45] Date of Patent: Jul. 12, 1988

[54] BICYCLIC AMIDE ACETAL-BASED CURE ACCELERATORS FOR AMINE CURING OF EPOXY COMPOSITIONS

[75] Inventor: Anil B. Goel, Worthington, Ohio

[73] Assignee: Ashland Oil, Inc., Ashland, Ky.

[21] Appl. No.: 70,990

[22] Filed: Jul. 8, 1987

[51] Int. Cl.$^4$ .............................................. C08G 59/68
[52] U.S. Cl. ........................................ 528/90; 528/94; 528/361; 528/407
[58] Field of Search ................. 528/90, 94, 361, 407

[56] References Cited

U.S. PATENT DOCUMENTS

| | | | |
|---|---|---|---|
| 3,642,649 | 2/1972 | Green et al. | 252/182 |
| 3,660,354 | 5/1972 | Uelzmann | 528/90 X |
| 4,161,575 | 7/1979 | Seymour et al. | 528/90 |
| 4,540,767 | 9/1985 | Goel et al. | 528/73 X |
| 4,594,397 | 6/1986 | Goel et al. | 528/85 X |
| 4,600,763 | 7/1986 | Goel | 528/111 |
| 4,614,786 | 9/1986 | Goel et al. | 528/73 X |
| 4,636,558 | 1/1987 | Goel | 528/363 |
| 4,704,409 | 11/1987 | Goel | 528/368 |

*Primary Examiner*—Earl Nielsen
*Attorney, Agent, or Firm*—John F. Jones

[57] ABSTRACT

A process for accelerating the cure rate of a mixture comprising an epoxy resin and an amine hardener comprising including in the mixture from 0.5% to 15% by weight of a catalyst which is the reaction product of a bicyclic amide acetal and ammonium thiocyanate and curing the resulting mixture at a temperature of from about abient temperature to about 120° C. is described.

17 Claims, No Drawings

BICYCLIC AMIDE ACETAL-BASED CURE ACCELERATORS FOR AMINE CURING OF EPOXY COMPOSITIONS

This invention relates to a process for the acceleration of cure of epoxy resins with amine hardeners by carrying out the cure in the presence of reaction products of a bicyclic amide acetal and ammonium thiocyanate catalysts.

Aromatic and aliphatic polyamines (primary, secondary, mixed primary and secondary, and combination of these with tertiary amines) and amido amines therefrom have been known as curing agents for epoxy resins. In order to improve the rate of cure of the amine curing epoxy compositions, various types of cure accelerators including (1) tertiary amines, (2) phenolics, (3) quaternary ammonium salts of strong acids, (4) metal salts of carboxylic acids, (5) boron trifluoride-amine and boron trifluoride-phenol complexes, and (6) mercaptans, thiocarbamic acids and thioether alcohols have been used in the prior art (See the article by Mika in "Epoxy Resins Chemistry and Technology," edited by May and Tanaka, Marcel Dekker, Inc. New York, 1973.) U.S. Pat. Nos. 3,265,664 and 3,271,350 describe the use of guanamine as a cure accelerator. U.S. Pat. Nos. 3,291,776 and 3,821,166 describe the use of thioethers and mercaptans. U.S. Pat. No. 2,909,494 describes the use of boron trifluoride-amine complexes as cure accelerators. U.S. Pat. No. 4,110,313 describes the use of dithiocarbamate salts, U.S. Pat. No. 4,195,153 describes the use of an amino alcohol as an accelerator for the amine curing of epoxy resins and U.S. Pat. No. 3,903,048 describes the use dimethyl dithiocarbamic acid dimethyl ammonium salt, bis(dimethyl thiocarbamyl) sulfide, tetramethylthiuram disulfide and the like as catalyst systems for lowering epoxy resin cure temperatures when cured with dicyandiamide. The use of a tertiary amine salt of thiocyanic acid as an amine cure accelerator has been shown in U.S. Pat. Nos. 3,6342,649 and 4,161,575. Quaternary ammonium (tetra alkylammonium) thiocyanate as accelerators for epoxy resins has been shown in U.S. Pat. No. 3,660,354 and the use of alkali and alkaline earth metal thiocyanate salts with aminoethylpiperazine as curing agent for epoxy resin curing has been shown in Japanese Patent No. 597823 [Chem. Abstr. 101 (20) 1723927]. Similarly, epoxy curing with polyamine/thiurea has been disclosed in Japanese Patent No. 48092437.

It is quite apparent that the rapid curing of epoxy resins has been the subject of much interest. Although the prior art cure accelerators improve the cure speed of epoxy resins when they are cured with amine hardeners, some limitations always have existed in the prior art. For instance, accelerators (such as mercaptans and thioethers) have unpleasant odors. Certain accelerators (such as boron trifluoride-amine and boron trifluoride-phenol complexes) are corrosive and the esters of phosphorus acid and metal carboxylates (such as stannous octoate) are moisture sensitive. Some of the accelerators are not very efficient and promote acceleration only mildly. In addition to this, most prior art accelerators either copolymerize with epoxy resins (for instance, phenolics, mercaptans, thiocarbamic acid) or catalyze the homopolymerization of epoxy resins. Examples of such catalysts are tertiary amines, boron trifluoride-amine salts and metal carboxylates. The use of the products of the reaction of bicyclic amide acetals with ammonium thiocyanate as cure accelerators in the polyamine/epoxy resin systems has not been disclosed previously.

The objective of this invention is to provide a new class of cure accelerators which are free from the aforementioned limitations which have been associated with the prior art accelerators and which do not cure epoxy resins themselves but provide high cure acceleration of the amine curing of epoxy resins.

I have discovered that the reaction products of ammonium thiocyanate with bicyclic amide acetals of Formula I act as excellent cure accelerators for epoxy resin compositions when cured with amine and amido amine curing agents.

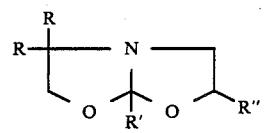

In Formula I, R, R' and R" independently can represent a hydrogen, an alkyl or an alkyl ether group having from 1 to 20 carbon atoms, an aryl or an aryl ether group having from 6 to 20 carbon atoms or an alkaryl group having from 7 to 20 carbon atoms.

The epoxy resins or polyepoxides suitable in the practice of this invention include those disclosed in U.S. Pat. Nos. 2,500,600 and 2,324,483 which are incorporated herein by reference. Preferred in this invention are 1,2-epoxy compounds having an epoxide equivalence greater than 1, that is to say, compounds containing more than one group of the formula:

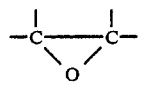

The 1,2-epoxide groups may be either terminal or inner ones. Particularly suitable terminal 1,2-epoxide groups are 1,2-epoxy ethyl or 1,2-epoxy propyl groups. The latter may be linked to an oxygen atom, that is to say, they are glycidyl ether or glycidyl ester groups. Compounds with inner epoxide groups usually contain the 1,2-epoxide group in an aliphatic chain or in a cycloaliphatic ring.

As epoxy compounds containing an inner 1,2-epoxy group there are suitable epoxidized diolefins, dienes, or cyclic dienes, such as 1,2,5,6-diepoxy hexane, 1,2,4,5-diepoxy cyclohexane, dicyclopentadiene diepoxide, dipentene diepoxide, vinyl cyclohexene diepoxide, epoxidized diolefinically unsaturated carboxylic acid esters, such as methyl-9,10,12,13-diepoxy stearate or the dimethyl ester of 6,7,10,11-diepoxyhexadecane-1,16-dicarboxylic acid. Furthermore, there may be mentioned epoxidized mono-, di-, or polyesters and mono-, di-, or polyacetals containing at least one cycloaliphatic 5-membered or 6-membered ring, to which at least two 1,2-epoxidized groups are linked.

A widely used class of polyepoxides which can be used in the present invention are the epoxy polyethers obtained by reacting a halogen containing epoxide or dihalohydrin, such as epichlorohydrin, epibromohydrin, 3-chloro-1,2-epoxyoctane, and the like with either a polyhydric phenol or a polyhydric alcohol.

I have found that when ammonium thiocyanate is mixed with a bicyclic amide acetal and heated at moderately elevated temperatures (generally below 150° C.), ammonia gas evolution occurs. Although this ammonia displacement reaction proceeds slowly at ambient temperatures, it proceeds rapidly at elevated temperatures. The stoichiometric reaction of one ammonium thiocyanate per bicyclic amide acetal results in products which show strong infrared spectral bands at about 2060 $cm^{-1}$, indicating the presence of thiocyanate groups in the reaction product. The isolated (preformed) bicyclic amide acetal thiocyanate complex catalysts, by themselves, have been found to be either inactive towards the curing of epoxy resins or exhibit extremely poor and slow reactivity at ambient to moderately elevated temperatures (below 120° C.). However, the thiocyanate salts of bicyclic amide acetals, when added to epoxy compositions containing amines and amido amine curing agents which may also contain other optionally known accelerators (such as phenolics, mercaptans and other thio group containing accelerators described in the prior art) cure rapidly at ambient temperatures, as well as at moderately elevated temperatures. The catalysts of this invention accelerate the epoxy curing reactions with amine hardeners to such an extent that small amounts (less than 15%, and preferably, from 0.5% to 10% by weight of the epoxy composition) of catalyst is needed to reduce the usual cure time several fold. For instance, the reaction of a liquid diglycidyl ether of Bisphenol-A with aminoethylpiperazine hardener (20% by weight of the hardener based on the weight of the total composition) which requires approximately 50 minutes at room temperature to give a gelled product, when carried out in the presence of about 5% by weight based on the total epoxy resin/amine composition of the bicyclic amide acetal thiocyanate salt (prepared by the reaction of ammonium thiocyanate with a bicyclic amide acetal of Formula I wherein R and R" represent hydrogen and R' represents an ethyl group), the curing occurs within six minutes of mixing at room temperature (about 8 times faster than the reaction without catalyst). Other important features of these catalysts are their capabilities to promote the cure acceleration of epoxy resins cured with amine hardeners containing other conventional known cure accelerators. The degree of cure rate acceleration of individual catalysts, as would be expected, may depend on the type of amine curing agent (basicity and nucleophilicity of the amine) used.

The type of amines useful in the curing of epoxy resins include mono-, di-, and polyamine containing primary, secondary, mixed primary and secondary amine and combinations of these with tertiary amines and the amido amines obtained therefrom by the reaction of them with carboxylic acids. The amines and amido amines may also contain other functionalities such as thioether, hydroxyl groups, urea and the like groups. Typical examples of such amines are butylamine, dodecylamines, cyclohexylamine, ethylene diamine, diethylene triamine, triethylene tetramine, tetraethylene pentamine, and the like, propylene diamine, dipropylene triamine and the like, cyclohexane dimethyl diamine, hexamethylene diamine, isophorone diamine, aminoethylpiperazine, bis(amino propyl) piperazine, piperidine, piperazine, morpholine, dimer acid diamine, alkanolamines such as ethanolamine, diethanolamine, N-alkyl alkanolamines, poly(alkylene ether) polyamines of molecular weights up to 10,000. Typical amido amines are those obtained by the reaction of di and polyamines such as ethylene diamine, diethylene triamine with higher carboxylic acids such as linoleic acid and fatty acids. These catalysts, in combination with amines, amido amines and amines with phenolics and mercaptans, may be used in epoxy formulations useful in applications such as coatings, adhesives, reaction injection molding, reinforced plastic, composites, potting compounds, tooling compounds, injection molding, sheet molding compounds and the like.

The catalysts of this invention may be dissolved or dispersed in the amine hardener and if desired, may be encapsulated in either thermoplastic materials or by reacting with reactive molecules such as isocyanate, epoxide and other techniques known in the art. The curable compositions of this invention may also include additives such as plasticizers, diluents, solvents, fillers, antioxidants, colorants and the like.

This invention is further illustrated in the following representative examples.

EXAMPLE 1

To 5.9 g of a bicyclic amide acetal of Formula I wherein R and R" represent hydrogen and R' represents an ethyl group was added 3.0 g of powdered ammonium thiocyanate under nitrogen atmosphere and the reaction mixture was heated at 100° C. for 30 minutes during which time ammonia gas evolution was observed. The resulting liquid was degassed under reduced pressure to ensure the complete removal of ammonia. The infrared spectrum of the liquid showed sharp band at 2060 $cm^{-1}$, indicating the presence of the thiocyanate group. This liquid was used as cure rate accelerator for the amine curing of epoxy resins. Typically, to a mixture of liquid diglycidyl ether of Bisphenol-A (DGEBPA, epoxy equivalent weight of 180–190) (12 g) and aminoethylpiperazine (2.5 g) was added 0.5 g of the thiocyanate complex of the bicyclic amide acetal described above. The resulting liquid was kept at room temperature and was found to gel within 6 minutes to give a thermoset polymeric composition.

EXAMPLE 2

This example which is for comparative purposes and is outside the scope of the present invention demonstrates that without the use of the cure accelerator of this invention, the epoxy resin when cured with amine hardener required much longer curing time. The procedure of Example 1 was followed using 12 g of DGEBPA epoxy resin and 3 g of aminoethylpiperazine. The resulting mixture was found to gel at room temperature in about 51 minutes.

EXAMPLE 3

This example which is also for comparison purposes and is outside the scope of this invention demonstrates that bicyclic amide acetal either alone or in combination with amine hardener is not an effective curing agent or cure accelerator. The diepoxide resin (DGEBPA) (12 g) and the bicyclic amide acetal of Example 1 (1 g) were mixed under nitrogen atmosphere and held at room temperature for curing. No gelation was observed over a period of two hours. In another experiment, the 12 g of diepoxide resin was mixed with 0.5 g of the bicyclic amide acetal and 2.5 g of aminoethylpiperazine and the solution was kept at room temperature. Gelation occurred in about 46 minutes.

EXAMPLE 4

This is also a comparative example which is outside the scope of this invention demonstrating that ammonium thiocyanate by itself is not a catalyst or a curing agent for epoxy resins. The liquid diglycidyl ether of Bisphenol-A (12 g) and 0.5 g of ammonium thiocyanate were mixed and kept at room temperature. No gelation was observed in two hours. After two hours at room temperature the mixture was heated at 100° C. for 30 minutes and again, no curing (gelation) was observed.

EXAMPLE 5

The procedure of Example 1 was followed using 12 g of DGEBPA, 2.5 g of diethylenetriamine and 0.5 g of the product of bicyclic amide acetal with ammonium thiocyanate (cure accelerator of Example 1). The resulting liquid was found to cure at room temperature in about 14 minutes. In another experiment, when the foregoing mixture was heated at 115° C., gelation occurred within 40 seconds to give the thermoset polymer. In contrast to this, when the 12 g of diepoxide resin mixed with 3 g of diethylenetriamine was kept at room temperature to cure, gelation did not occur until about 65 minutes had transpired.

EXAMPLE 6

The procedure of Example 1 was followed using 12 g of DGEBPA, 1.5 g of poly(propylene oxide) diamine (molecular weight of 400), 0.76 g of bis(aminopropyl) piperazine and 0.27 g of the catalyst of Example 1. The resulting liquid was found to gel at 115° C. in about 2 minutes and 10 seconds. In comparison, when the above reaction mixture without the catalyst was heated at 115° C., gelation occurred in 4 minutes and 15 seconds.

EXAMPLE 7

A liquid catalyst was prepared by reacting 5.2 g of a bicyclic amide acetal of Formula I wherein R and R" represent hydrogen and R' represents a methyl group with ammonium thiocyanate (3.1 g) at 100° C. for 30 minutes, followed by degassing under reduced pressure. To a mixture of DGEBPA (12 g) and 2.5 g of aminoethylpiperazine was added 0.45 g of this catalyst, and the resulting reaction solution was kept at room temperature to cure. Gelation occurred within 7 minutes to give a thermoset polymer.

EXAMPLE 8

The procedure of Example 7 was followed using 6 g of the DGEBPA, 1.25 g of diethylene triamine and 0.24 g of the catalyst of Example 7. Gelation of the solution at room temperature occurred in 21 minutes.

EXAMPLE 9

To a mixture of 6 g of DGEBPA, 1.5 g of poly(propylene oxide) diamine (molecular weight about 400) and 0.7 g of bis(aminopropyl) piperazine was added 0.25 g of the catalyst of Example 7 and the reaction solution was heated at 115° C. Gelation occurred in 2 minutes and 20 seconds.

EXAMPLE 10

To a solution of trimethylol ethane triglycidyl ether (5.1 g) and 4.1 g of poly(propylene oxide) triamine (molecular weight of 400) was added 0.2 g of the catalyst of Example 7 and the reaction solution was heated at 120° C. and gelation occurred within 3 minutes and 30 seconds at this temperature. In comparison, when a mixture of the triepoxy resin (5.1 g) and the triamine (4.2 g) without the catalyst was heated at 120° C., gelation occurred in 6 minutes.

EXAMPLE 11

This example demonstrates that the thiocyanate complexes of bicyclic amide acetals when mixed with epoxy compositions as cure accelerators may be used in applications such as epoxy coating. In a typical experiment, to a solution of 10 g of liquid diglycidyl ether of Bisphenol-A (epoxy equivalent weight of 180 to 190), 2 g of the diglycidyl ether of poly(propylene oxide) glycol (epoxy equivalent weight about 320) and aminoethylpiperazine (2.5 g) was added 0.5 g of the catalyst of Example 1. The solution was applied on a zinc phosphatized steel plate in the form of 1-2 mils thick coating. This coating was then cured in an air convection oven at 110° C. for 5 minutes to give a non-tacky, very glossy, transparent coating with a pencil hardness of 2H. The cured coating showed 100% adhesion (tested by using Tape Adhesion Test method) and was found to have better than 70 in./lbs. of reverse impact strength.

EXAMPLE 12

A mixture of 4.4 g of a bicyclic amide acetal of Formula I wherein R represents hydrogen, R' represents an ethyl group, and R" represents a phenyl group and 1.5 g of ammonium thiocyanate was heated at 110° C. for 30 minutes and degassed under reduced pressure. An 0.7 g portion of this catalyst was added to a solution of 12 g of liquid diglycidyl ether of Bisphenol-A and 2.6 g of aminoethylpiperazine. The resulting solution was found to gel in 7 minutes and 40 seconds to give a solid thermoset polymer.

I claim:

1. The process for accelerating the cure of a mixture comprising an epoxy resin and an amine hardener comprising including in the mixture from 0.5% to about 15% by weight of a catalyst which is the reaction product of a bicyclic amide acetal and ammonium thiocyanate and curing the resulting mixture at a temperature in the range of from about ambient temperature to about 150° C.

2. The process of claim 1 wherein the bicyclic amide acetal is of the formula I

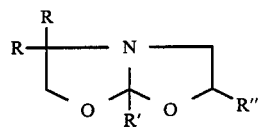

wherein R, R' and R" independently represent hydrogen, an alkyl group having from 1 to 20 carbon atoms, an alkyl ether group having from 1 to 20 carbon atoms, an aryl group having from 6 to 20 carbon atoms. An aryl ether group having from 6 to 20 carbon atoms on an alkaryl group having from 7 to 20 carbon atoms.

3. The process of claim 2 wherein the epoxy resin is a compound having more than one group of the formula

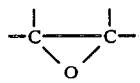

4. The process of claim 3 wherein the amine hardener is a member selected from the group consisting of butyl amine, dodecyl amines, cyclohexyl amine, ethylene diamine, diethylene triamine, triethylene tetramine, tetraethylene pentamine, propylene diamine, dipropylene triamine, cyclohexane dimethyl diamine, hexamethylene diamine, isophorone diamine, aminoethylpiperazine, bis(amino propyl) piperazine, piperidine, piperazine, morpholine, dimer acid diamine, ethanol amine, diethanolamine, N-alkyl alkanol amines, poly(alkylene ether) polyamines of molecular weights up to 10,000, and amido amines obtained by the reaction of a polyamine with a higher carboxylic acid.

5. The process of claim 4 wherein the epoxy resin is the diglycidyl ether of Bisphenol-A.

6. The process of claim 4 wherein the epoxy resin is trimethylol ethane triglycidyl ether.

7. The process of claim 5 wherein the bicyclic amide acetal is one of Formula I wherein R and R″ represent hydrogren and R′ represents an ethyl group.

8. The process of claim 7 wherein the amine hardener is aminoethylpiperazine.

9. The process of claim 7 wherein the amine hardener is diethylene triamine.

10. The process of claim 7 wherein the amine hardener is poly(propylene oxide) diamine plus bis(amino propyl) piperazine.

11. The process of claim 5 wherein the bicyclic amide acetal is one of Formula I wherein R and R″ represent hydrogen and R′ represents a methyl group.

12. The process of claim 11 wherein the amine hardener is aminoethylpiperazine.

13. The process of claim 11 wherein the amine hardener is diethylene triamine.

14. The process of claim 6 wherein the bicyclic amide acetal is one of Formula I wherein R and R″ represent hydrogen and R′ represents a methyl group.

15. The process of claim 14 wherein the amine hardener is poly(propylene oxide) triamine.

16. The process of claim 5 wherein the bicyclic amide acetal is one of Formula I wherein R represents hydrogen, R′ represents an ethyl group and R″ represents a phenyl group.

17. The process of claim 6 wherein the amine hardener is aminoethylpiperazine.

* * * * *